United States Patent [19]

Rhee et al.

[11] Patent Number: 4,637,252
[45] Date of Patent: Jan. 20, 1987

[54] TEST INSTRUMENT

[75] Inventors: Chong-Kon Rhee, Broadview Heights, Ohio; David M. McKibben, Cleveland, Ohio; Jeffrey N. Bibbee, Lake Jackson, Tex.

[73] Assignee: The Uniroyal Goodrich Tire Company, Akron, Ohio

[21] Appl. No.: 672,654

[22] Filed: Nov. 19, 1984

Related U.S. Application Data

[63] Continuation of Ser. No. 421,749, Sep. 23, 1982, abandoned.

[51] Int. Cl.[4] .................................................. G01N 19/04
[52] U.S. Cl. ..................................... 73/150 A; 73/827
[58] Field of Search ................. 73/827, 838, 150 A; 24/523, 569; 248/349

[56] References Cited

U.S. PATENT DOCUMENTS

| | | | |
|---|---|---|---|
| 1,763,128 | 6/1930 | Bolland | 24/569 |
| 2,509,328 | 5/1950 | Anderson | 24/523 |
| 2,611,165 | 9/1952 | Straka | 24/523 |
| 3,214,971 | 2/1965 | Hammond | 73/150 A |
| 3,444,732 | 5/1969 | Robbins | 73/150 A |
| 3,821,892 | 7/1974 | Säberg | 73/150 A |
| 4,117,627 | 10/1978 | Slingerland | 248/349 |
| 4,263,811 | 4/1981 | Shaw | 73/827 |

Primary Examiner—Charles Frankfort
Assistant Examiner—Denis E. Corr
Attorney, Agent, or Firm—J. J. Januszkiewicz; H. F. Pepper, Jr.

[57] ABSTRACT

A tack measuring device and method wherein two specimens are brought into abutting contact under a predetermined load, after which the contact is maintained momentarily. The specimens are then separated within a second time interval. A load cell measures the force as a function of time and the tack is measured in terms of velocity times the force integrated over the second time interval.

22 Claims, 11 Drawing Figures

TEST INSTRUMENT

This is a continuation of application Ser. No. 421,749, filed 9/23/82, now abandoned.

BACKGROUND OF THE INVENTION

This invention relates to an instrument and method for measuring tack and more particularly to a portable tack tester.

There is a widespread need for a more efficient and reliable measurement of the physical property of tack of elastomeric materials including rubber materials. Tack is defined as the ability of two uncured rubber or elastomeric surfaces to adhere together upon contact under moderate pressure. Tack has also been defined as the force per unit area required to separate two like pieces of rubber or elastomeric material after pressing them together. This is often called autohesion. Tack is to be distinguished from stickiness which is the force per unit width required to separate a piece of rubber or elastomeric compound from some other material, usually steel. Most of the present instruments commercially available measure tack by determining the pull required to separate one sample surface from another by the force exerted in a direction that is perpendicular to the surfaces of the sample. Another instrument measures the peeling forces where one sample of rubber material is peeled away from a second sample in a direction parallel to the adhered surfaces with the result expressed as force per unit width of the strip. Both of these instruments and their corresponding methods measure the maximum force per unit area or per unit width. In preparing samples for testing in these above instruments, it is required that samples or specimens be cut by a die cutting machine to assure the operator that the edges of the sample to be tested be perpendicular to each other. The present invention is directed to a portable tack tester that eliminates the need for precise cutting out of samples wherein the tack tester can measure tack directly at a work station or taken to the processing line as on a tread tuber line. This invention includes a new and novel mechanism for securing the sample. A unique feature of the invention is that in its measurement of tack, the instrument takes into account the time value to thereby express the tack measurement in terms of energy. In contrast to force per unit area the applicant's units of measurement are in terms of energy per unit contact area. The significance of this method is that there is a strong correlation between the tack measurement and the factory experience for quality control of factory production in a factory environment.

SUMMARY OF THE INVENTION

The present invention contemplates the measuring of tack of elastomeric material wherein two spaced specimens of material are moved into abutting contact under a predetermined load for a predetermined dwell time interval and thence separating the specimens by breaking the contact therebetween in a second time interval which is measured as Energy per unit contact area. A load cell device measures the force exerted to load and separate the specimens and provides a tack reading that is based on the energy expended during such time interval.

DETAILED DESCRIPTION

Figure 1:
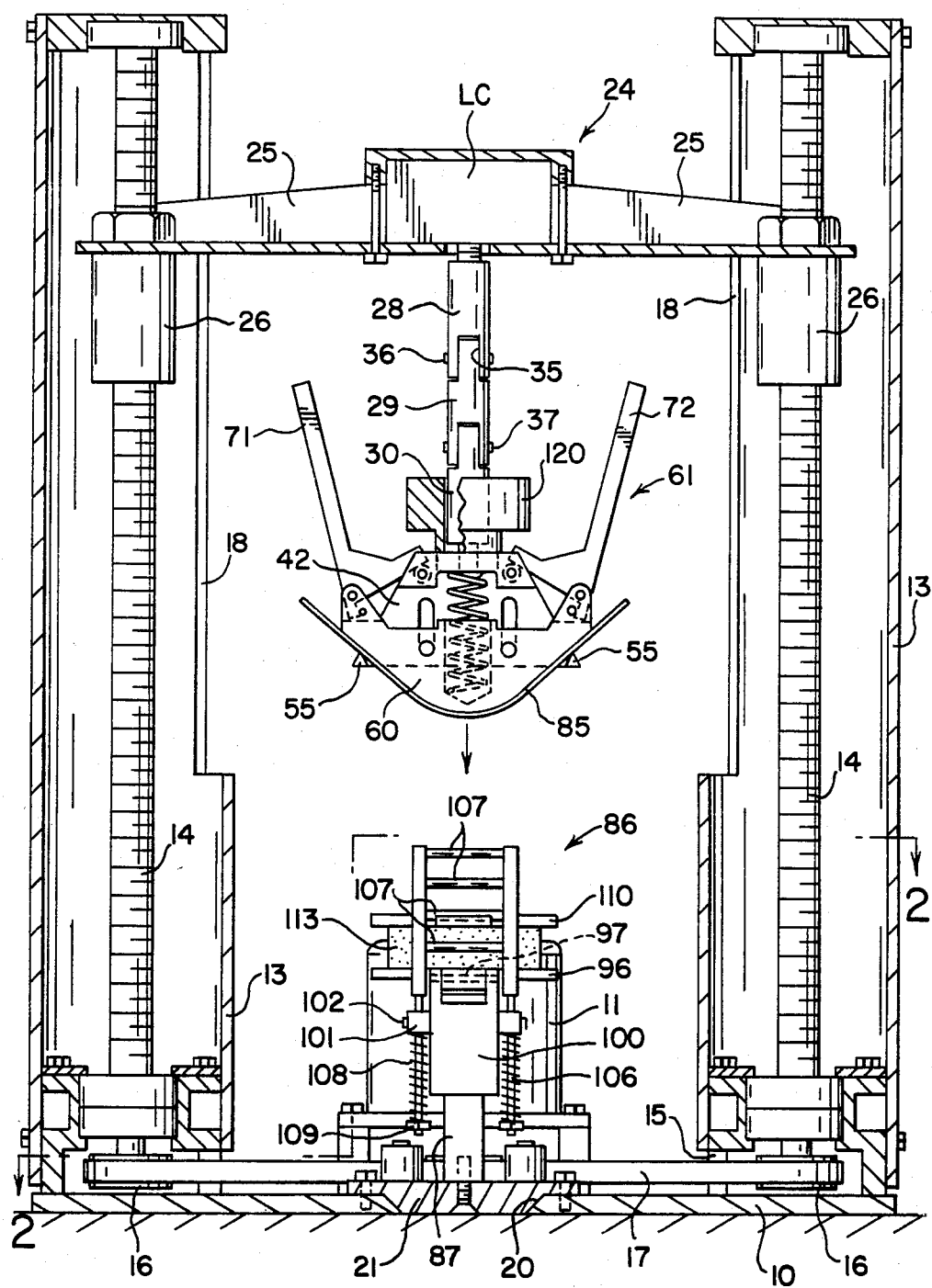
FIG. 1 is a front elevational view of a tack testing machine of a preferred embodiment of the invention.
Figure 2:
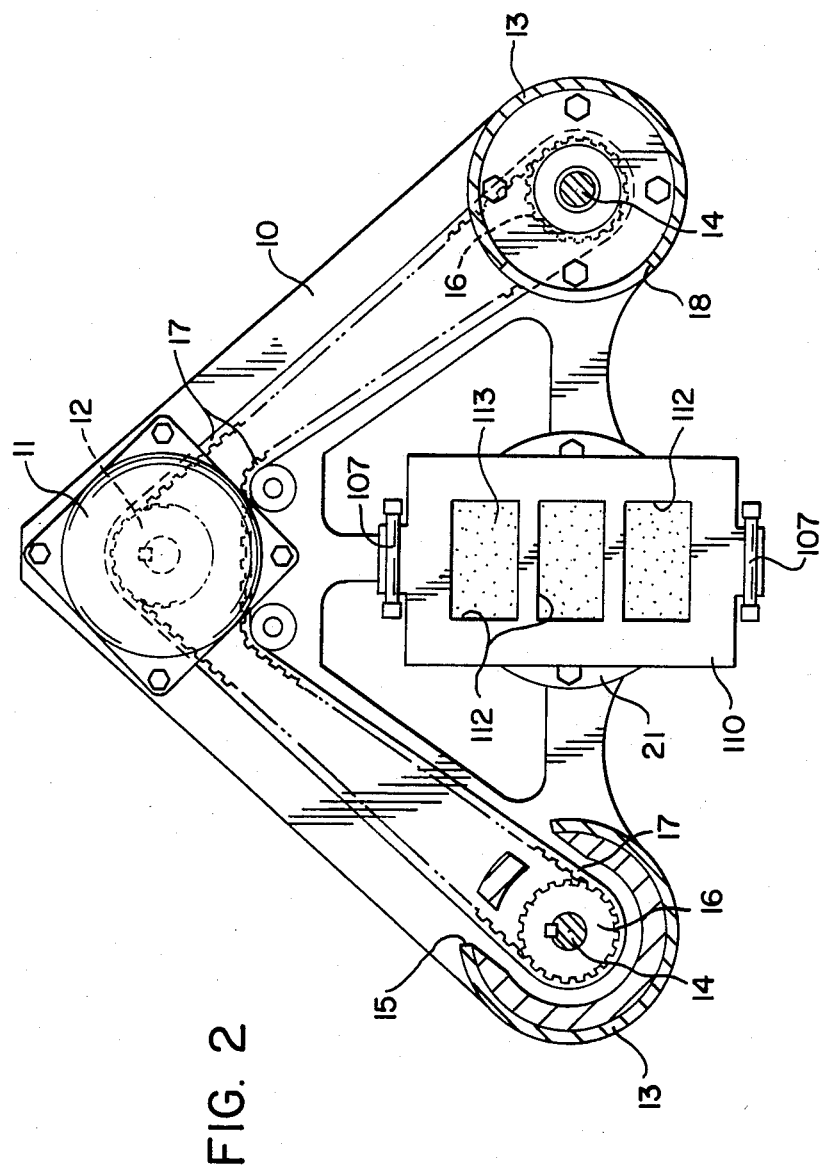
FIG. 2 is a cross-sectional plan view of the tack testing machine taken in line 2—2 of FIG. 1.

Referring now to the drawings, wherein like reference numerals designate like or corresponding parts throughout the several views, there is shown in FIG. 1 a base or base plate 10 generally triangular in shape in plan view. As seen in FIG. 2, a stepping motor 11 is mounted on the rear portion thereof, having an output shaft connected to a drive pulley 12. Mounted at the respective sides of base 10 is a tubular housing 13. The respective housings 13 are alike and accordingly only one will be described. A threaded shaft 14 has its ends journaled for rotation in housing 13. The shaft 14 and the housing 13 act as a frame member to support a carriage to be described, which carriage moves relative to such frame member in a manner to be described. The lowermost end portion of housing 13 below the journaling of shaft 14 is recessed as at 15 in the direction of pulley 12, such that a pulley 16 keyed to shaft 14 will permit a timing belt 17 to substantially encompass such pulley and be directed rearward toward drive pulley 12.

Base 10 between pulleys 16 is recessed as at 20, (FIG. 1) such that the tack testing instrument with base 10 can be placed onto a specimen to be tested. A circular plate member 21 having a conical portion is received by the recess 20 and is suitably secured to the base 10. A specimen holder, to be described, is mounted on such plate member 21. Housing 13 has a longitudinally extending slit or recess 18 extending from the upper-end portion thereof to below the intermediate portion thereof. A carriage 24 having a pair of laterally extending brackets 25 which extend through the respective slits 18 are suitably secured to nuts 26 which in turn are threadedly engaged to the threaded shaft 14. Such shaft 14 and the housing 13 act as a support or frame member for the carriage 24. Carriage 24 moves up or down as controlled by the rotation of threaded shafts 14 which in turn is controlled by the energization of stepping motor 11 with its connection to pulleys 16 via timing belt 17. A load cell LC is mounted on carriage 24.

Figure 6:
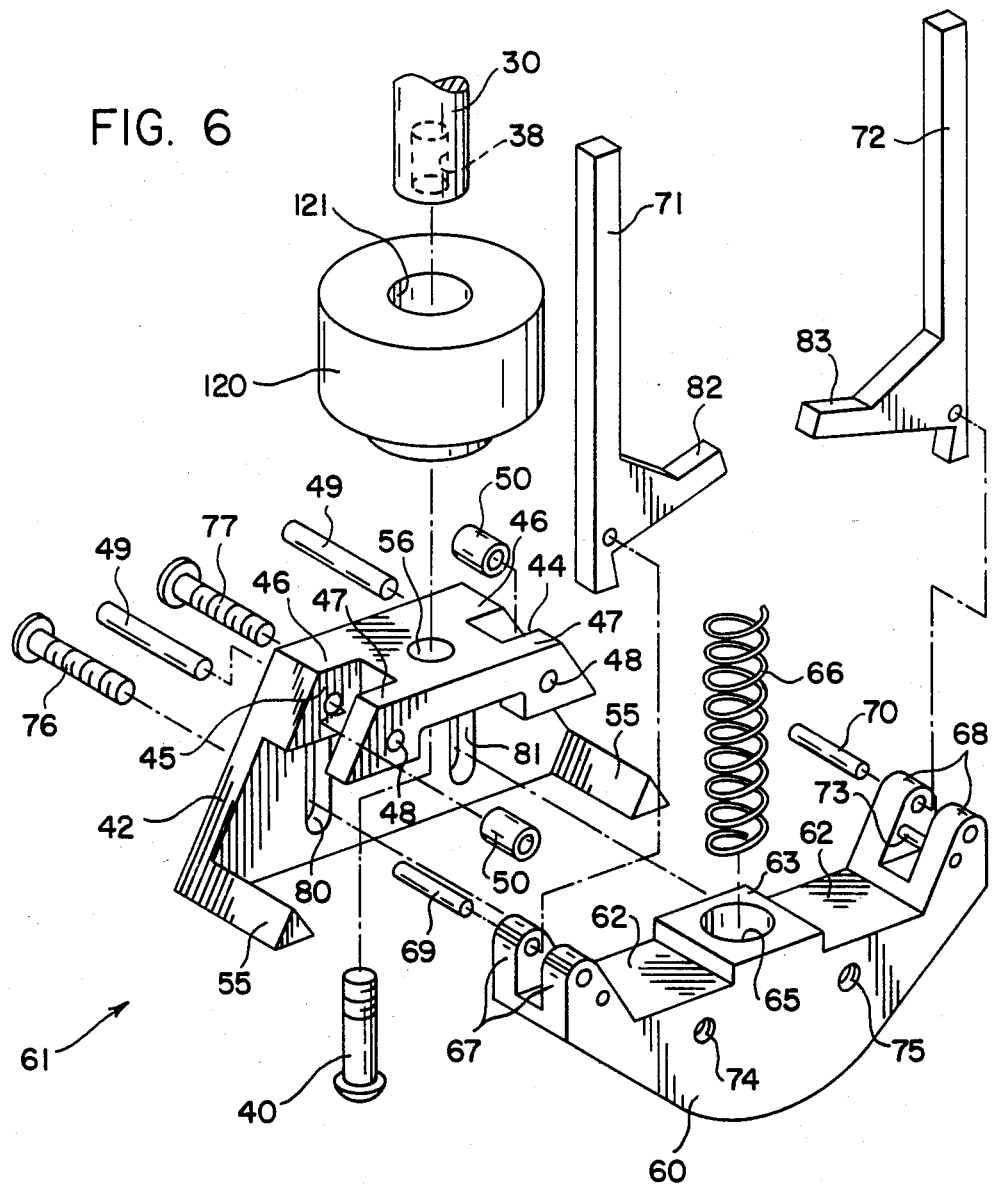
FIG. 6 is an exploded view of the upper portion of the mechanism for holding the specimen.

Suitably connected to carriage 24 for movement therewith via cylindrical rods 28, 29 and 30 is an upper specimen holder having a first block member 42 that is trapezoidal in shape. Uppermost rod 28 is threadably connected to the load cell LC in carriage 24 while the lower end of rod 28 is centrally recessed as at 35 for pivotal connection to the upper end of intermediately located rod 29 as at 36. Lower rod 30 is pivotally connected to rod 29 as at 37. The lower end portion of rod 30 has a threaded bore 38 (FIG. 6) to receive a bolt 40. The block member 42 of such specimen holder has an upper forwardly extending portion that is recessed at both side portions as at 44 and 45 to provide pairs of spaced abutments 46 and 47. The respective projecting abutments 46 and 47 have horizontally extending aligned bores 48 receiving pins 49. In assembling such pins 49 into such bores 48, a sleeve 50 is first inserted between the abutments 46 and 47 in alignment with such bores 48 before the pins 49 are slid into position. The respective lower edges of trapezoidal block member 42 of the upper specimen holder 61 have triangular shaped abutments 55 extending outwardly therefrom. A bore 56 extends vertically through the upper portion of block member 42 such that bolt 40 extends therethrough and retains such block member 42 to rods 28, 29 and 30. Bolt 40 is of such a length as to provide a clearance between block member 42 and rod 30 for a purpose to be described. Cooperative with first block member 42 is a second block member 60 which together define the upper specimen holder 61.

Figure 3:
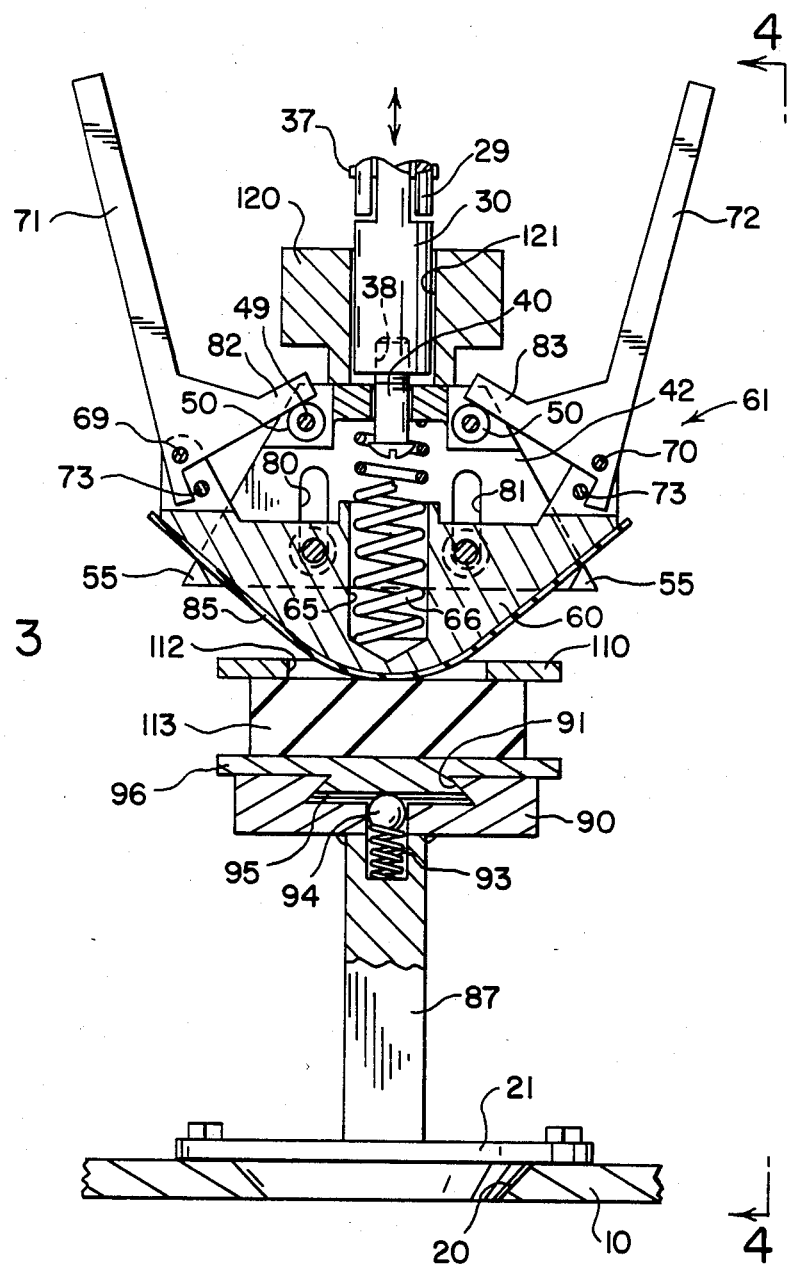
FIG. 3 is an enlarged view of the mechanism for holding the specimen of the tack testing machine shown in FIG. 1 with a portion thereof shown in cross-section.

Block member 60 (FIG. 6) of specimen holder 61 is an arcuately shaped block having a pair of spaced upper planar surface 62 with an abutment 63 therebetween. Abutment 63 has a bore 65 therein, receiving a compression spring 66 which biases the arcuate portion into contact with the laterally spaced abutments 55. The respective outer upper ends of block member 60 have a clevis 67–68 receiving pins 69–70 for connection to L-shaped lever members 71–72 for pivoting such lever members 71–72. A second pin 73 (as seen in FIG. 3) is mounted in the respective clevises 67 and 68 below the location of pins 69–70 but parallel thereto. Block member 60 of upper specimen holder 61 has a pair of spaced threaded bores 74 and 75 receiving threaded bolts 76 and 77, which bolts 76 and 77 ride in vertically extending slots 80 and 81 in trapezoidal shaped block member 42. This permits the vertical movement of block member 60 relative to block member 42.

Figure 5:
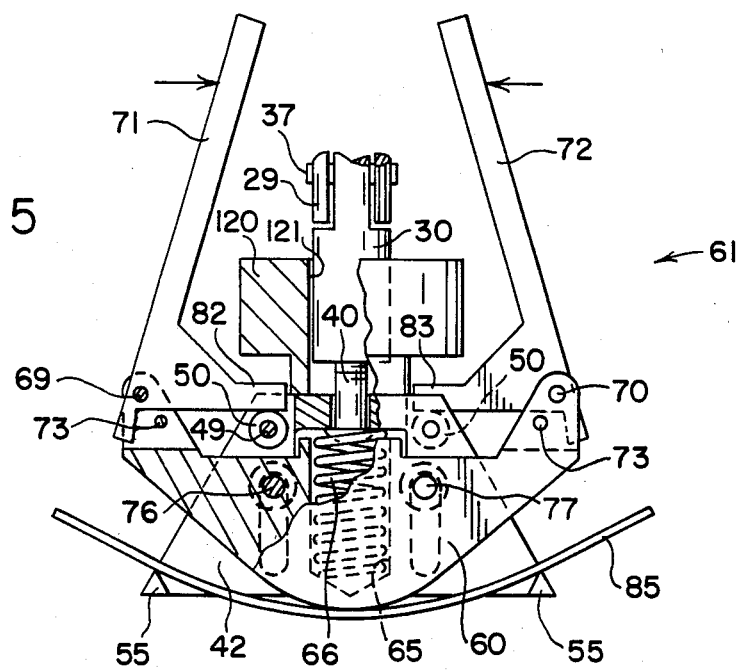
FIG. 5 is an enlarged cross-sectional view of the upper portion of the mechanism for holding the specimen with the clamp means in a released condition.

The respective L-shaped lever members 71–72 pivotally mounted on block member 60 as on pins 69 and 70 have inwardly extending abutments 82 and 83 which ride on the respective sleeves 50. Rotation of the upper ends of lever members 71–72 toward each other about pins 69 and 70 will move the lower specimen holder portion 60 upwardly relative to the triangular shaped abutments 55 providing a clearance space between such abutments 55 and the lower arcuate surface of block member 60 so as to permit the insertion of a sample along the arcuate surface and into such clearance space, as shown in FIG. 5. Release of the lever members 71 and 72 will move the block member 60 downwardly relative to abutments 55 to clamp the specimen 85 in position due to the biasing action of spring 66 as seen in FIGS. 1 and 3.

Figure 4:
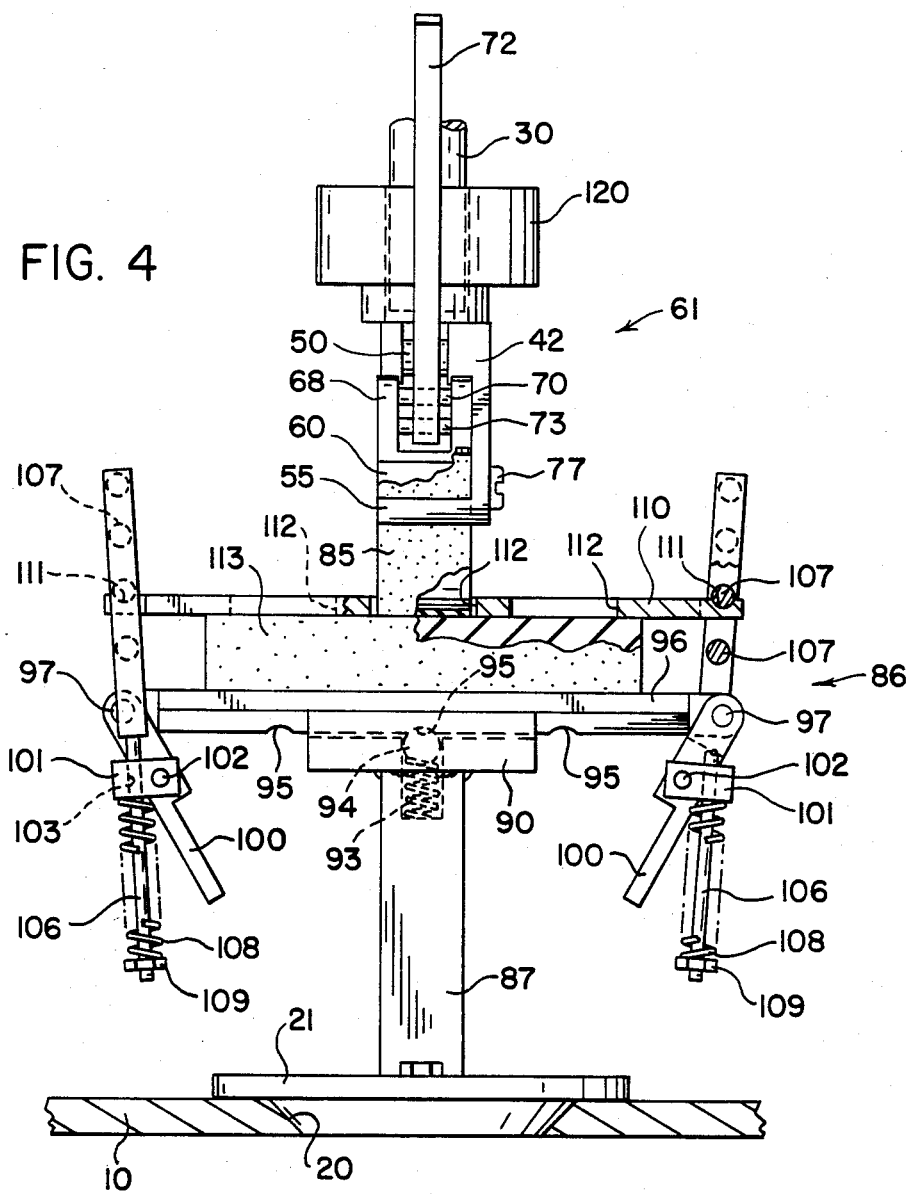
FIG. 4 is an enlarged side elevational view of the mechanism for holding the specimen taken on line 4—4 of FIG. 3.

As seen in FIGS. 1 and 4, a lower specimen holder 86 has a post 87 suitably secured to the circular plate 21 which in turn is suitable connected to the base 10. Vertically extending post 87 has a horizontally disposed block 90 with a dovetail groove 91 extending therethrough (FIG. 3). A bore in block 90 and post 87 receives a spring 93 which biases a ball 94 located directly above it into one of a plurality of recesses 95 (FIG. 4) in the lower surface of a slide member 96 thus acting as a detent. Slide member 96 has a dovetail lower portion which is slidingly received by the groove 91 to guide the slide member 96 on block 90. The respective outer ends of slide member 96 has a bore for receiving a pin 97. Pivotally mounted on each pin 97 on each end of slide member 96 is a plate member 100 having a bifurcated upper end portion that receives such pin 97. Only one side of lower specimen holder 86 will be described, it being understood that like elements are located on the other side of slide member 96, which elements are designed with like numerals. The respective intermediate side portions of plate member 100 each have a block 101 pivotally mounted thereon as at 102. Each block 101 has a bore 103 extending vertically therethrough. A latch member or means is slidably mounted on each side pair of blocks 101 and includes a pair of vertically moveable rods 106 slidably received by bores 103. The upper portion of the pair of rod 106 which is square in cross-section includes cross rods 107. That portion of each rod 106 located below block 101 has a spring 108 encompassing it with the lower end portion of spring 108 seated on a nut 109 threaded thereon. Such latch member or latch means is cooperative with a flat plate 110 which has groove 111 along the respective outer edge portions for receiving one of the cross rods 107. Plate member 110 has a plurality of laterally spaced rectangular openings 112 for the purpose of exposing a sample of material to be tested. A sample of material 113 to be tested is placed on the upper flat surface of slide member 96, afterwhich the plate member 110 is placed over the sample as depicted by FIG. 4. The respective latch means are then used to secure the sample by swinging or pivoting the pair of vertically moveable rods 106 about pins 97. As seen in FIG. 4, the rods 106 on the left has the lower portion pivoted in a counterclockwise direction so that one of the rods 107 engages the groove or recess 111 on plate member 110 while its corresponding plate member 100 is swung counter clockwise so that pivot 102 is also swung beyond the pin 97 thereby moving the plate member 100 beyond dead center. The spring 108 exerts a downward pressure on rod 106 and the rod 107 to clamp the plate member 110 into abutting engagement with the sample 113. Simultaneously with this action plate member 100 and rod 106 on the right side of the apparatus as seen in FIG. 4 is operated in a similar manner to positively secure the sample 113 in position for testing. It will be observed in the right hand side of FIG. 4, that when plate member 100 is pivoted counter clockwise about pivot 97, that the sample will be released when pin 102 is moved counter clockwise a sufficient distance past the vertical line passing through pivot or pivot pin 97.

Figure 10:
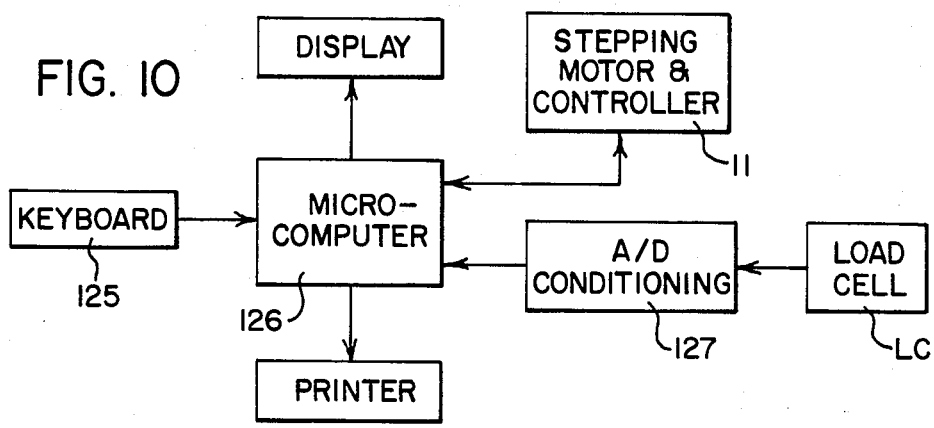
FIG. 10 is a diagrammatic representation of a portion of the system of FIG. 1.
Figure 11:
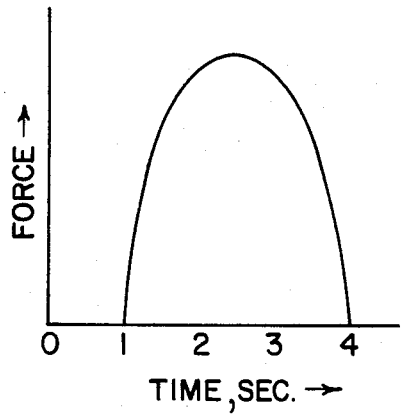
FIG. 11 is a chart illustrating the force measured as a function of time during the period of time that the samples of material are being separated when tack is being measured.

In the operation of the apparatus as described above, the operator places a flat sample of material on the slide member 96 and clamps the material in place with the latch means as described above through the pivotal movement of the plate members 100 which has rods 107 engaging the recesses 111 on the top plate 110. The slide member 96 is moved rectilinearly on block 90 to allow ball 94 to engage one of the recesses 95 which aligns one of the openings 112 and the sample of material exposed thereby for contact with the specimen of material to be positioned on the upper specimen holder 61. To load the upper specimen holder 61, a strip of material 85 to be tested is placed around the arcuate portion of holder 61 as disclosed by FIG. 5. It will be noted that in FIG. 5 the levers 71 and 72 are biased toward each other which action pivots the levers 71 and 72 about pivot means 69 and 70 while abutments or extensions 82 and 83 of levers 71 and 72 engage collars 50 to maintain the specimen holder 61 upwardly relative to trapezoidal shaped block member 42 and abutments 55. When the specimen 85 is in position, the lever members 71 and 72 are released and will move the specimen holder 61 with the specimen 85 downwardly due to the action of spring 66 until the sample or specimen 85 engages the laterally spaced abutments 55. It should be noted that the cylindrically shaped weight 120 with a central bore 121 (FIG. 6) is assembled onto rod 30 prior to securing of screw 40 thereto which provides a predetermined force between the specimens 85 and 113. With the specimens 85 and 113 retained in their respective holders as described above, the operator actuates the stepping motor 11 by depressing the appropriate start key on keyboard 125 which through microcomputer 126 sends a signal to energize the stepping motor 11. A load cell designated LC in FIGS. 1 and 10 is continually sensing the load on the rods 28, 29, 30 and the upper specimen holder 61. Assuming a 20 psi pressure from weight 120, the load cell via analogue to digital unit 127 continually sends this loading weight as a signal along with the weight of the rod and the specimen holder 61 to the microcomputer. The load cell LC senses the 20 psi pressure from weight 120 which together with the weight of the specimen 85, weight of specimen holder 61, weight of rods 28, 29, 30 and bolt 40 represents the total weight thereon and is referred to as the dead weight. Such dead weight is the total weight registered on the load cell LC and is the predetermined weight from which the loading on the sample will be calculated. This dead weight or predetermined weight will be reduced by 20% for the loading weight in the example described. When stepping motor 11 is energized, its output via belt 17 rotate gear pulleys 16 which in turn rotates threaded shafts 14 thereby moving carriage 24 downwardly relative to the frame member (shaft 14 and housing 13), moving rods 28, 29, 30 therewith along with specimen 85 and specimen holder 61. When the specimen 85 makes contact with specimen 113, the load cell accordingly registers this change with the microcomputer which instantly senses the change in the dead weight, which in our example is a 20% reduction in initial dead weight. Due to the fact that the load cell LC no longer senses the weight of the rods 28, 29, 30 and the bolt 40 but only the weight of the specimen 85, the weight 120, and the weight of the specimen holder 61. Physically when contact is made between the specimens, the rods 28, 29 and 30 have sufficient clearance as seen in FIG. 3 to permit continued travel relative to the weight 120 and specimen holder 61. That is, bolt 40, rods 28, 29 and 30 continue to travel downwardly with the carriage 24. At the instant of sensing the 20% reduction in dead weight, the microcomputer as a control means allows the stepping motor 11 to run a pre-set time interval beyond the contact point and then allows the stepping motor to sit idle for a pre-set time interval, which is referred to as the dwell time. The stepping motor is then energized by the control means and reversed in its rotation upon lapse of such dwell time thereby separating the specimen 85 from the specimen 113. The dwell time or the first time intervals can be pre-set by the microcomputer and is programmable. Such dwell time includes the interval of time that the microcomputer first senses a reduction in weight and the idle interval to where the stepping motor is reversed. The second interval of time as illustrated by FIG. 11 begins when motor 11 is reversed to where the microcomputer or the control means no longer senses the reduction in weight. As an example of the time element involved expressed as a one second dwell time, such time period includes [1] three tenths (0.3) of a second covering the period of time that the microcomputer senses a change or a reduction in initial dead weight, during which time there is a downward movement of rods 28, 29 and 30 with the weight stationary, [2] four tenths (0.4) of a second of waiting or inaction time, and [3] three tenths (0.3) of a second covering the period of time that there is still a clearance space where the microcomputer signals the stepping motor to reverse its direction and there is actual rotation of the threaded shafts 14—14 before the load cell senses a pick-up of the dead weight due to the elimination of the clearance space between the upper specimen holder 61 and the head of the bolt 40. During the test time the microcomputer or control means records the tack as energy (inch-pounds) per unit area (square inches). In this process of measuring tack in terms of the energy per unit contact area the test conditions utilize 1 second of dwell time. The microcomputer or the control means energizes the stepping motor 11 to provide as an example a contact pressure of 20 psi at a 10 inch per minute separation rate which is substantially an instantaneous separation as this is equivalent to 1 inch per 6 seconds or 0.16 inch per second. As a further example of the units used to calculate the tack, the energy is the integral of Force times differential of distance wherein E (energy) equals $\int Fdx = \int (Fdx/dt) \cdot dt$ which is $(dx/dt) \int F dt$. The fraction of $dx/dt$ is velocity of separation where $dx$ is distance and where $dt$ is time. The data obtained by this measurement correlate with hand tack tests and can be used for the quality control of factory production. Since the microcomputer has the speed of separation stored in its memory, and it takes force measurements at small equal time intervals (FIG. 11), the energy integral is easily calculated by a summation method. The cross-sectional area is also a parameter stored in the microcomputer memory, so that it can carry out the division necessary to calculate energy/unit area. As an example consider the following data in Table I.

TABLE I

| Material Code | Comparison of Tack of Five Different Materials | | |
|---|---|---|---|
| | HandTack* Ranking | Tack (Force/area) pounds/inch$^2$ | Tack (Energy/area) in-pounds/inches$^2$ |
| A | 1 | 5.6 | 44.7 |
| B | 2 | 8.6 | 32.0 |
| C | 3 | 4.0 | 4.3 |
| D | 4 | 1.6 | 0.9 |
| E | 5 | 1.9 | 0.7 |

*hand-tack ranking 1 represents the best tack in the group tested.

As indicated by the data from this table there is a direct correlation between the hand-tack testing of samples and those measured utilizing the energy concept as detailed above whereas tack as measured in force per unit of area have poor correlation with the tack as measured and ranked 1 through 5.

In lieu of using a weight 120, the microcomputer can be used to detect as previously described a change in the loading on the load cell LC when contact is made. The microcomputer can be set to stop the stepping motor 11 whenever the load cell registers an input to the microcomputer of 20 psi. In this instance the loading is done by the stepping motor. The dwell time for the stepping motor in the example chosen again is 1 second. After the lapse of time, the microcomputer provides an input signal to the stepping motor to reverse its direction to raise the carriage 24 and separate the materials being tested. In this instance the interval of time is a second interval and which the energy of separation is measured.

A modification of the above described apparatus includes the elimination of the lower specimen holder 86 such that the circular plate 21 is also removed, leaving a bore 20 on the base 10. In this condition, the tack testing apparatus can be carried to the site at which the measurements are to take place and the apparatus is positioned on the material to be tested, so as to expose a portion of the material through the bore 20. The upper specimen holder 61 is lowered until the specimen 85 comes in contact with the material to be tested that is exposed by the bore 20. The procedure for testing is identical to that described in the first embodiment except that the apparatus rests on the specimen to be tested.

Figure 7:
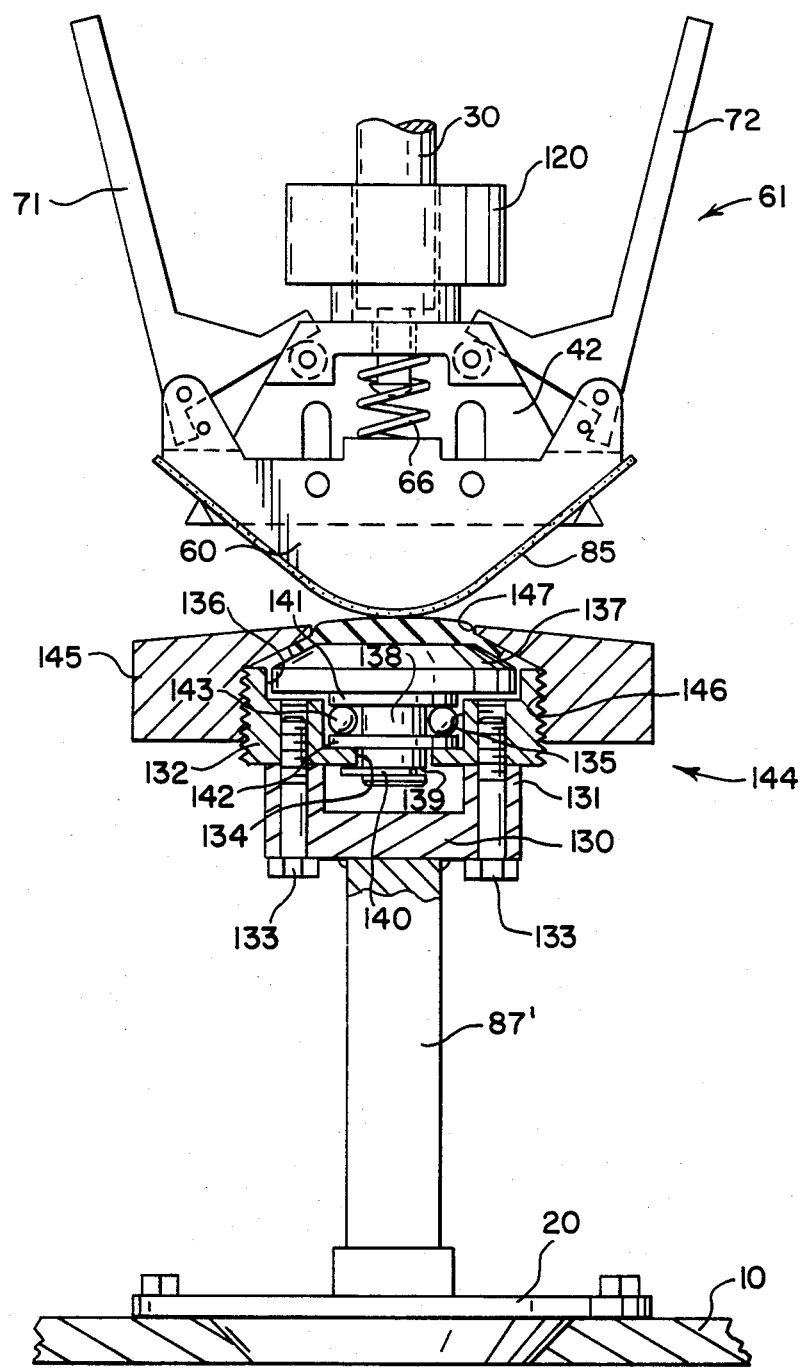
FIG. 7 is an enlarged front elevational view of a modified form of a specimen holding clamp.
Figure 8:
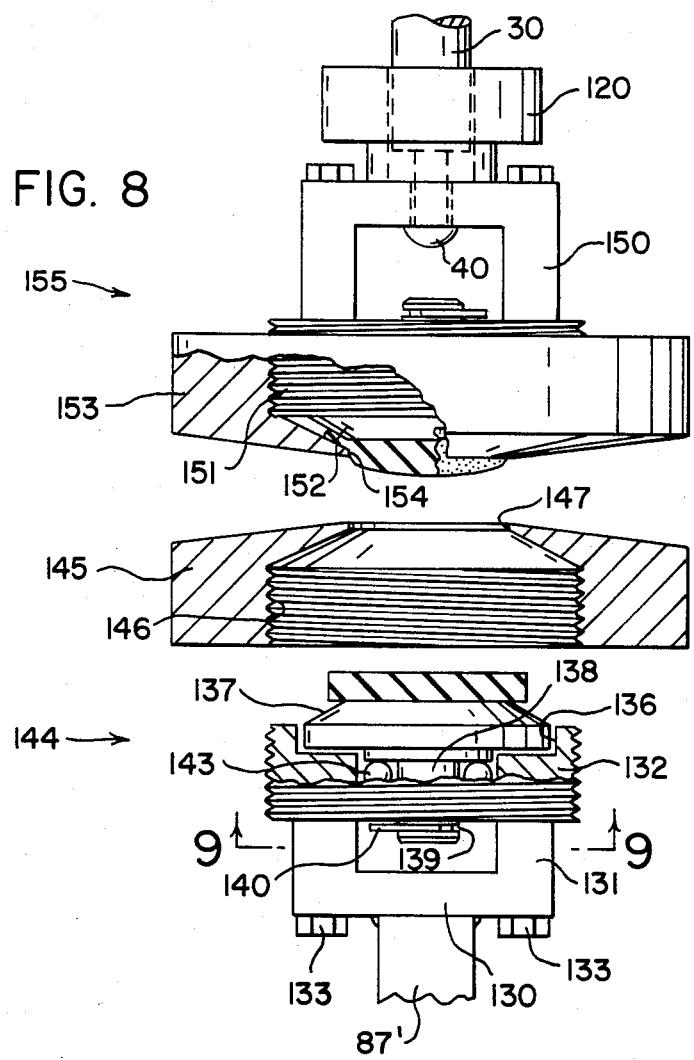
FIG. 8 is an enlarged front elevational view partly broken away, of a modified form of specimen holding means.
Figure 9:
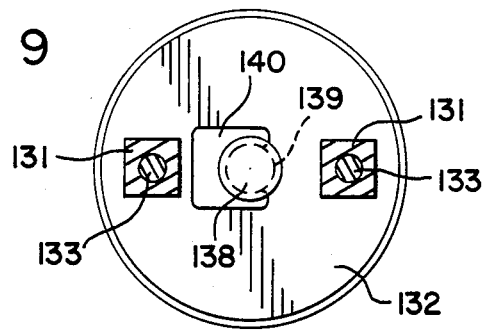
FIG. 9 is a cross-sectional view of the specimen holding means taken along lines 9—9 of FIG. 8.

A further modification is shown in FIG. 7 and the lower portion of FIG. 8. Herein the post or support 87' is attached to the base 10 in the same manner as the first embodiment. The upper end of post or support 87' has a cylindrical shaped support 130 with a pair of vertically extending projections or abutments 131 extending upwardly therefrom. An annular member 132 is mounted on top of the laterally spaced projections or abutments 131 and interconnected to the support 130 by bolts 133 extending through the projections 131. The outer cylindrical surface of annular member 132 is threaded and has centrally disposed stepped bore with a small bore portion 134, an intermediate size bore portion 135, and a large bore portion 136. An annular support with a frusto-conical shaped specimen support 137 and a depending stem 138 is received by such stepped bore. The stem 138 has an annular recess 139 on its lower end portion receiving a clip 140 to retain such stem 138 and the frusto-conical support 137 within the stepped bore. Prior to the assembling of the annular support into externally threaded annular member 132, thrust washers 141, 142 and thrust bearings 143 are assembled on stem 138 as the stem is inserted into bore 135, after which clip 140 is secured to the stem to lock such conical support 137 and stem 138 to the annular ring 132. A sample or specimen of rubber material is placed on the frusto-conical support 137 and thence an inverted annular shaped retaining member 145 which is internally threaded as at 146 is threaded onto annular ring 132 to captively secure the specimen within the lower specimen holder 144. A central opening 147 in retaining member 145 exposes the specimen of material for contact by the specimen of the upper specimen holder as seen in FIG. 7.

A further modification of the invention is shown in FIG. 8 wherein the rod 30 with the annular weight 120 is connected via bolt 40 to a U-shaped support 150. Suitably connected to support 150 is a threaded cylindrical plug 151 with a frusto-conical shaped specimen support 152. An annular internally threaded retainer 153 is threaded onto cylindrical plug 151 to captively secure a sample or specimen of material as in the last described embodiment. Retainer 153 has a central opening 154 to expose the sample and is in alignment with the lower specimen holder 144. A cylindrical plug 151 is constructed in the same manner as the corresponding parts in lower specimen holder 144. The support 150, plug 151 and retainer 153 form a upper specimen holder 155. The operation of the upper specimen holder 155 in cooperation with lower specimen holder 144 can be identical as that described in the first embodiment. A variation on the operation is to eliminate the weight 120 and providing a loading via the stepping motor 11 as measured by the load cell and the microprocessor described above. Such action eliminates the need for any clearance space between the bolt 40 and the support 150 as described above.

It will be apparent that, although a specific embodiment and certain modification of the invention have been described in detail, the invention is not limited to the specifically illustrated and described constructions since variations may be made without departing from the principles of the invention.

We claim:

1. The process of measuring tack of elastomeric compositions, comprising the steps of bringing two specimens of elastomeric stock into abutting contact to define a contact area under an initial contact pressure, maintaining said contact pressure between said two specimens for a predetermined first time interval which is a dwell time, separating said contact between said specimens within a second time interval at a predetermined separation rate, measuring the tack as energy per unit contact area required to separate said stock specimens by integrating the force to separate said specimens over said second time interval for complete separation to occur, and multiplying said integral by said separation rate and dividing the product by contact area to give tack.

2. The process of measuring tack as set forth in claim 1 wherein said first time interval is one second or less.

3. The process of measuring tack as set forth in claim 2 wherein said force to separate said specimens is a variable force over said second time interval.

4. The process of measuring tack of an elastomeric composition including rubber comprising the steps of bringing a first specimen and a second specimen into abutting contact with each other to define a contact area therebetween that is under a predetermined contact pressure; maintaining said contact for a predetermined dwell time interval; separating said contact between said specimens at a predetermined separation rate until separation is completed between specimens to define a second time interval; said dwell time is a predetermined pre-set time; measuring the force required to separate said specimens during said second time interval; and integrating said force required to separate said specimens over said second time intervals to give an integral; and multiplying said integral by said separation rate, and dividing the product by said contact area to give tack.

5. The process of measuring tack as set forth in claim 4 wherein said dwell time is a predetermined pre-set time of less than one second.

6. The process of measuring tack of an elastomeric composition including rubber comprising the steps of bringing a first specimen and a second specimen into abutting contact with each other to define a contact area therebetween; maintaining said contact for a predetermined first time interval; separating said contact between said specimens at a predetermined separation rate until separation is completed between specimens defining a separation time interval which is a second time interval, while simultaneously measuring the force required to separate said specimens; integrating said measured force over said second time interval to provide an integral; and multiplying said integral by said separation rate and dividing such product by said contact area to provide a tack reading.

7. A portable apparatus for measuring tack of elastomeric material comprising a base, a frame member mounted on said base, said base having an aperture for exposing a sample of material as said base rests on said sample, specimen holding means with a specimen thereon mounted on said frame member for movement to and from said base, a stepping motor mounted on said base, control means connected to said stepping motor for energizing said stepping motor for moving said specimen holding means to and from said base, said aperture being in alignment with said specimen holding means, force measuring means operatively connected to said specimen holding means providing an output signal to said control means that is proportional to the force being measured in response to the loading between said specimen on said specimen holding means and said sample when in contact, said control means responsive to said output signal for energizing said stepping motor to initiate a predetermined separation rate between said sample and said specimen on said specimen holding means, and said control means operative to integrate said output signal over said time interval to give an integral, multiplying said integral by said separation rate and dividing the product by said contact area provided between said two specimens to give tack.

8. A portable apparatus as set forth in claim 7 wherein a second specimen holding means is mounted on said base member in alignment with said first mentioned specimen holding means to hold a specimen, said specimens move into contact upon actuation of said stepping motor for moving said first mentioned holding means toward said second specimen holding means.

9. An apparatus for measuring tack between two specimens of elastomeric material, comprising a pair of vertically aligned and spaced specimen holding means with specimens therein, positioning means for effecting relative movement of said holding means to bring said specimens held by said holding means into contact over a predetermined contact area and to detach said specimens, load cell means connected to one of said specimen holding means to register force exerted between specimens and to provide an output signal that is proportional to said force developed as a function of time, control means to command said relative movement of said holding means, said control means operatively connected to said load cell to receive said output signal and integrate said output signal as a function of time between an interval of time that contact is maintained between said specimens over the contact area between specimens thereby measuring the tack therebetween as energy per unit contact area, said interval of time that contact is maintained between specimens is measured as two intervals of time with one of said intervals representing a time period from initial contact between specimens to where separation of specimens begins, a second of said two intervals of time begins when separation of specimen begins and is the full time for separation to occur defining a second time interval.

10. An apparatus for measuring tack as set forth in claim 9 wherein the sum of said two intervals of time is a maximum of ten seconds.

11. An apparatus for measuring tack between two specimens of elastomeric material, comprising a pair of vertically aligned and spaced specimen holding means with specimens therein, moving means for effecting relative movement of said holding means to bring said specimens held by said holding means into contact over a predetermined contact area, load cell means connected to one of said specimen holding means to register force exerted between specimens and to provide an output signal that is proportional to said force developed as a function of time, control means operatively connected to said load cell to receive said output signal and integrate said output signal as a function of time between an interval of time that contact is maintained between said specimens over the contact area between specimens thereby measuring the tack therebetween as energy per unit contact area, said interval of time that contact is maintained between specimens is measured as two intervals of time with one of said intervals representing a time period from initial contact between specimens to where separation of specimens begins, a second of said two intervals of time begins when separation of specimen begins and is the full time for separation to occur defining a second time interval; the sum of said two intervals of time is a maximum of ten seconds; one of said specimen holding means comprises a slide member cooperative with clamping means for securing a sample therebetween, said clamping means includes a cover plate having a plurality of laterally spaced apertures to selectively present different portions of the specimen into alignment with the other one of said specimen holding means, and said slide member has a plurality of detents to register selected ones of said apertures in alignment with said other specimen holder.

12. An apparatus for measuring as set forth in claim 11 wherein said other specimen holder includes a pair of cooperative members operative to hold a sample in an arcuate contour.

13. An apparatus for measuring as set forth in claim 12 wherein said means for moving said other specimen holder of said specimen holding means includes a carriage moveable toward and away from said one of said specimen holding means, said carriage has said load cell means mounted therein, elongated rod means rigidly interconnecting said load cell to said other specimen holder to apply a load directly on said specimens as monitored by said load cell.

14. An apparatus for measuring as set forth in claim 12 wherein said means for moving said holding means includes a carriage moveable toward and away from said one specimen holding means, said carriage has said load cell means mounted therein, elongated rod means interconnecting said load cell to said other specimen holder to apply a load directly on said specimens, and said interconnection between said rod means and said other specimen holder includes a clearance space to permit overtravel of said carriage and said rod means upon contact of said specimens of said specimen holders wherein a predetermined weight is thereby exerted between said specimens during such overtravel.

15. An apparatus for measuring as set forth in claim 14 wherein said overtravel and pressure exerted between specimens as well as said separation rate of contct is controlled by said control means.

16. A specimen holder for a tack tester comprising a first member with an upper portion and a lower pair of spaced abutments, an arcuately shaped second member mounted on said first member for limited rectilinear movement thereon, said arcuately shaped second member having an arcuately shaped lower surface where spaced portions contact said spaced abutments, biasing means interconected between said first and second members for biasing said arcuately shaped lower surface of said second member into abutting contact with said abutments, lever means distinct from and operative between said first and said second members for separating the spacing between said arcuate shaped lower surface of said second member and said spaced abutments of said first member to facilitate the locating of a sample thereon, said lever means comprises a pair of levers, each of said levers is generally L-shaped and includes an elongated member with a laterally extending arm, the juncture portion between said elongated members of each of said levers and its corresponding said arms is pivotally mounted on said second member, said arms rest on a roller journaled on said first member to provide a movement between said first and second member on selective pivotal movement of said lever means about their respective pivotal mountings.

17. A specimen holder for a tack tester comprising support means for supporting a first specimen to expose it to contact with another specimen for tacky engagement, said support means having an annular member fixedly mounted thereon, thrust bearing means mounted in the central aperture of said annular member, said thrust bearing means having an upper flat surface that is operative as a specimen support member for supporting said first specimen thereon, said annular member being externally threaded, an annular ring member being internally threaded for threaded attachment to said annular member, said ring member having an annular reduced upper inner portion for cooperative engagement of said first specimen supported by said specimen support member of said thrust bearing means to thereby facilitate the testing of tack between both specimens.

18. An apparatus for measuring tack of rubbery or polymeric compositions, comprising a pair of vertically aligned and spaced specimen holding means, moving means for effecting relative movement of said holding means to bring specimens held by said holding means into contact over a predetermined area, load cell means connected to one of said specimen holding means to register force exerted between specimens and to provide an output signal that is proportional to said force developed, control means operatively connected to said load cell to receive said output signal and integrate said output signal as a function of time between an interval of time that contact is maintained between said specimens over the contact area between specimens for ultimately measuring the tack therebetween as energy per unit contact area, said contact between specimens is measured as two intervals of time, one of said intervals of time represents a time period from initial contact between specimens to where separation of specimens is to occur, said second interval of time is the full time for separation to occur, said one interval of time is one second or less, said two intervals of time is a maximum time of ten seconds, one of said specimen holding means comprises a slide member cooperative with clamping means for securing a specimen thereon, said clamping means includes a cover plate having a plurality of laterally spaced apertures to selectively present different portions of the specimen into alignment with the other one of said specimen holding means, and said slide member has a plurality of detents to register selected ones of said apertures in alignment with said other specimen holder.

19. An apparatus for measuring as set forth in claim 18 wherein said other specimen holder includes a pair of cooperative members operative to hold a sample in an arcuate contour.

20. An apparatus for measuring as set forth in claim 19 wherein said means for moving said holding means includes a carriage moveable toward and away from said one specimen holding means, said carriage has said load cell means mounted therein, elongated rod means rigidly interconnecting said load cell to said other specimen holder to apply a load directly on said specimens as monitored by said load cell.

21. An apparatus for measuring as set forth in claim 19 wherein said means for moving said holding means includes a carriage moveable toward and away from said one specimen holding means, said carriage has said load cell means mounted therein, elongated rod means interconnecting said load cell to said other specimen holder to apply a load directly on said specimens, and said interconnection between said rod means and said other specimen holder includes a clearance space to permit overtravel of said carriage and said rods upon contact of said specimens of said specimen holders wherein a predetermined weight is thereby exerted between said specimens during such overtravel.

22. An apparatus for measuring as set forth in claim 21 wherein said overtravel and pressure exerted between specimens as well as said separation rate of contact is controlled by said control means.

* * * * *